United States Patent [19]

Boigegrain et al.

[11] Patent Number: 5,656,648
[45] Date of Patent: Aug. 12, 1997

[54] POLYSUBSTITUTED 2-AMINO-THIAZOLE DERIVATIVES

[75] Inventors: Robert Boigegrain, Assas; Roger Brodin, Montpellier; Daniel Frehel, Toulouse; Danielle Gully, Saubens; Jean-Charles Molimard, Saint-Gely Du Fesc; Dominique Olliero, Montpellier, all of France

[73] Assignee: SANOFI, Paris, France

[21] Appl. No.: 474,548

[22] Filed: Jun. 7, 1995

Related U.S. Application Data

[62] Division of Ser. No. 196,751, Feb. 15, 1994, abandoned.

[30] Foreign Application Priority Data

Feb. 19, 1993 [FR] France .................. 93 01 941

[51] Int. Cl.[6] .................. A01K 31/425
[52] U.S. Cl. .................. 514/371; 514/311
[58] Field of Search .................. 514/371, 311

[56] References Cited

U.S. PATENT DOCUMENTS 5,189,049  2/1993  Frohel .................. 514/377

*Primary Examiner*—Robert Gerstl
*Attorney, Agent, or Firm*—Jacobson, Price, Holman & Stern, PLLC

[57] ABSTRACT

The invention relates to the use of a compound of formula:

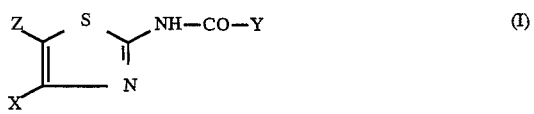

in which Y represents a 3-quinolyl group or a 2-indolyl group of formula:

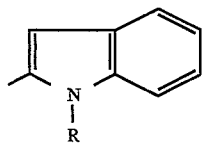

in which:

X is chosen from 4-chloro-2,6-dimethoxyphenyl, 2,6-dimethoxy-4-methylphenyl, 2,4,5-trimethoxyphenyl, 4-methyl-2,3,6-trimethoxyphenyl, 2,6-dimethoxy-4-ethylphenyl, 2,4,6-trimethoxy-5-chlorophenyl, 2,4,6-trimethoxy-3-pyridyl, 2,4-dimethoxy-6-methyl-3-pyridyl, 6-chloro-2,4-dimethoxy-5-pyrimidinyl, 2,4,6-trimethoxy-5-pyrimidinyl, 5-chloro-2,4-dimethoxyphenyl, 5-chloro-2-methoxy-4-methylphenyl, 2,5-dimethoxy-4-methylphenyl, 4-trifluoromethyl-2,6-dimethoxyphenyl, 2,4-dimethoxy-5-methylphenyl, 5-ethyl-2,4-dimethoxyphenyl and 2,4-dimethoxyphenyl groups;

Z represents H, a $C_1$–$C_4$-alkyl or a benzyl;
for combating complaints whose treatment necessitates a stimulation of the cholecystokinin receptors by a total or partial agonist effect.

3 Claims, No Drawings

POLYSUBSTITUTED 2-AMINO-THIAZOLE DERIVATIVES

This is a divisional of application Ser. No. 08/196,751, filed Feb. 15, 1994 now abandoned.

The present invention relates to the use of thiazole derivatives for the preparation of medicinal products. It also relates to new thiazole derivatives, to a process for preparing them and to medicinal products containing them.

More especially, the present invention relates to new agonists of cholecystokinin (CCK) receptors in the pancreatic amylase test.

CCK is a peptide widely distributed in the brain, in particular in the cortex, striatum, hippocampus, ventral tegmentum, septum and hypothalamus.

CCK is also secreted at peripheral level by the small intestine; its action manifests itself, in particular, in a stimulation of vesicular contraction, an increase in biliary secretion, a control of pancreatic enzyme secretion, an action on gastric contraction and an action on intestinal motility. It might act in some cases on arterial blood pressure and influence immune systems.

CCK coexists in some central neurons with dopamine. It also participates in mechanisms involving acetylcholine, GABA (4-aminobutyric acid), sertonin, opioids, somatostatin, substance P and ion channels.

Its administration causes physiological modifications, namely palpebral ptosis, hypothermia, hypoglycemia and catalepsy, and behavioural modifications, namely depression of locomotor function, diminution of exploratory activity, analgesia, modification of learning ability, modification of sexual behaviour and satiety.

A CCK-receptor agonist can hence be used as a medicinal product in the treatment of certain eating disorders, obesity and diabetes, disorders of emotional, sexual and mnestic behaviour, schizophrenia, psychoses, Parkinson's disease and various disorders of the gastrointestinal system (Drugs of the future, 1992, 17 (3), 197–206).

CCK-receptor agonists are described in the literature. For example, some products having such properties are described in EP-A-0,383,690, WO 90/06,937 and EP-A-0,376,849.

Patent Application EP-A-0,432,040 describes acylaminothiazoles having an affinity for the CCK A receptor and the CCK B receptor. Some of the compounds claimed in Application EP-A-0,432,040 have been described, in particular, as CCK A- and CCK B-receptor antagonists.

It has now been found, surprisingly, that a series of acylaminothiazoles, some of which are included in EP-A-0,432,040, possess a potent agonist activity at CCK receptors, and are hence useful for the preparation of CCK-agonist medicinal products.

Thus, according to one of its aspects, the subject of the invention is the use of N-(2-thiazolyl)-indolecarboxamides or N-(2-thiazolyl)quinolinecarboxamide of formula:

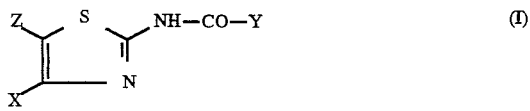

in which Y represents a 3-quinolyl group or a 2-indolyl group of formula:

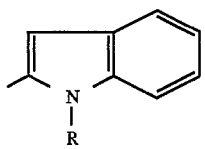

in which:

R is hydrogen, an acetyl group or a group $CH_2COOR'$, $R'$ being hydrogen or a $C_1$–$C_4$-alkyl;

X is a (hetero)aryl radical chosen from 4-chloro-2,6-dimethoxyphenyl, 2,6-dimethoxy-4-methylphenyl, 2,4,5-trimethoxyphenyl, 4-methyl-2,3,6-trimethoxyphenyl, 2,6-dimethoxy-4-ethylphenyl, 2,4,6-trimethoxy-5-chlorophenyl, 2,4,6-trimethoxy-3-pyridyl, 2,4-dimethoxy-6-methyl-3-pyridyl, 6-chloro-2,4-dimethoxy-5-pyrimidinyl, 2,4,6-trimethoxy-5-pyrimidinyl, 5-chloro-2,4-dimethoxyphenyl, 5-chloro-2-methoxy-4-methylphenyl, 2,5-dimethoxy-4-methylphenyl, 4-trifluoromethyl-2,6-dimethoxyphenyl, 2,4-dimethoxy-5-methylphenyl, 5-ethyl-2,4-dimethoxyphenyl and 2,4-dimethoxyphenyl groups;

Z represents H, a $C_1$–$C_4$-alkyl or a benzyl; with the limitation that Z is necessarily hydrogen when X is a phenyl radical substituted simultaneously at positions 2 and 6 or when X is a 3-pyridyl radical substituted simultaneously at positions 2 and 4 or when X is a 5-pyrimidinyl radical substituted simultaneously at positions 4 and 6;

as well as their pharmaceutically acceptable salts and their solvates, for the preparation of medicinal products intended for combating pathologies whose treatment necessitates a stimulation by a total or partial agonist effect at the cholecystokinin receptors.

Among the compounds of formula (I) above, some are not described in the literature and hence constitute a further subject of the present invention.

Thus, according to another of its aspects, the invention relates to new acylaminothiazole derivatives of formula:

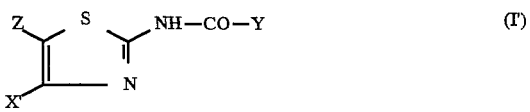

in which Y represents a 3-quinolyl group (a) or a 2-indolyl group (b) of formula:

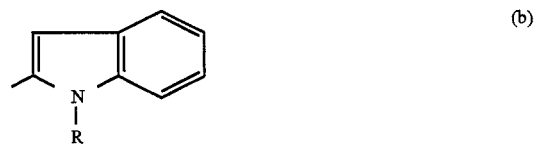

in which:

R is hydrogen, an acetyl group or a group $CH_2COOR'$, $R'$ being hydrogen or a $C_1$–$C_4$-alkyl;

X' is a (hetero)aryl radical chosen from 4-chloro-2,6-dimethoxyphenyl, 2,6-dimethoxy-4-methylphenyl, 2,4,5-trimethoxyphenyl, 4-methyl-2,3,6-trimethoxyphenyl, 2,4,6-trimethoxy-5-chlorophenyl, 2,4,6-trimethoxy-3-pyridyl, 2,4,6-trimethoxy-5-pyrimidinyl, 2,4-dimethoxy-6-methyl-3-pyridyl, 6-chloro-2,4-dimethoxy-5-pyrimidinyl, 5-chloro-2,4-dimethoxyphenyl, 5-chloro-2-methoxy-4-methylphenyl, 2,5-dimethoxy-4-methylphenyl, 4-trifluoromethyl-2,6-dimethoxyphenyl, 2,4- dimethoxy-5-methylphenyl and 5-ethyl-2,4-dimethoxyphenyl groups;

Z represents H, a $C_1$-$C_4$-alkyl or benzyl; with the limitation that Z represents H when X is a phenyl radical substituted simultaneously at positions 2 and 6 or when X is a 3-pyridyl radical substituted simultaneously at positions 2 and 4 or when X is a 5-pyrimidinyl radical substituted simultaneously at positions 4 and 6; as well as their salts and their solvates.

The addition salts of these compounds are those obtained with inorganic or organic acids and bases: the pharmaceutically acceptable, non-toxic salts are preferred, but other salts which can be used for isolating or purifying the compounds of formula (I') are also a subject of the invention.

The compounds of formula (I') in which Y represents a group (b) wherein R is hydrogen or a $CH_2COOH$ group are especially advantageous.

The compounds of formula (I') in which Z represents a hydrogen or a methyl are especially advantageous.

The compounds of formula (I') in which Y represents a radical (b) wherein R is hydrogen or a $CH_2COOH$ group, Z represents a hydrogen or a methyl and X' represents an aryl radical chosen from 4-chloro-2,6-dimethoxyphenyl, 5-chloro-2,4-dimethoxyphenyl, 5-chloro-2-methoxy-4-methylphenyl, 2,6-dimethoxy-4-methylphenyl, 2,4-dimethoxy-5-methylphenyl and 2,4,5-trimethoxyphenyl groups (Z necessarily being a hydrogen when X' represents a 4-chloro-2,6-dimethoxyphenyl or 2,6-dimethoxy-4-methylphenyl group) are preferred.

Among the compounds of formula (I') above, N-[4-(4-chloro-2,6-dimethoxyphenyl)-2-thiazolyl]-1-(carboxymethyl)indole-2-carboxamide and its pharmaceutically acceptable salts and solvates, in particular the hydrochloride, N-[4-(5-chloro-2,4-dimethoxyphenyl)-2-thiazolyl]-1H-indole-2-carboxamide and its pharmaceutically acceptable salts and solvates, N-[4-(5-chloro-2,4-dimethoxyphenyl)-5-methyl-2-thiazolyl]-1H-indole-2-carboxamide and its pharmaceutically acceptable salts and solvates, N-[4-(5-chloro-2,4-dimethoxyphenyl)-5-methyl-2-thiazolyl]-1-(carboxymethyl)indole-2-carboxamide and its pharmaceutically acceptable salts and solvates, in particular the trifluoroacetate, N-[4-(5-chloro-2-methoxy-4-methylphenyl)-2-thiazolyl]-1H-indole-2-carboxamide and its pharmaceutically acceptable salts and solvates, N-[4-(2,6-dimethoxy-4-methylphenyl)-2-thiazolyl]-1H-indole-2-carboxamide and its pharmaceutically acceptable salts and solvates, in particular the hydrochloride monohydrate, N-[4-(2,4-dimethoxy-5-methylphenyl)-5-methyl-2-thiazolyl]-1H-indole-2-carboxamide and its pharmaceutically acceptable salts and solvates, and N-[4-(2,4,5-trimethoxyphenyl)-5-methyl-2-thiazolyl]-1H-indole-2-carboxamide and its pharmaceutically acceptable salts and solvates, are especially preferred.

The subject of the invention is also a process for the preparation of the compounds of formula (I'), characterized in that an acid of formula (II)

$$Y'-COOH \quad\quad (II)$$

in which Y' represents a 3-quinolyl radical (a)

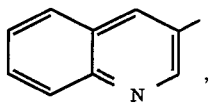 (a)

a 2-indolyl radical (b°)

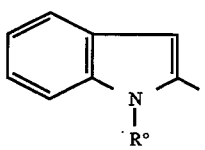 (b°)

or a 2-indolinyl radical (c°)

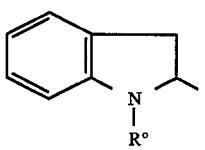 (c°)

R° being an N-protecting group or a group $CH_2COOR''$, where R'' is a $C_1$-$C_4$-alkyl; or alternatively a functional derivative of the said acid (II), is condensed with a 2-aminothiazole of formula:

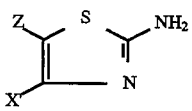 (III)

in which X' and Z are defined above, in the presence of a base, to obtain a compound of formula (I''):

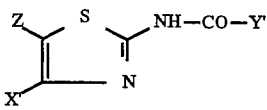 (I'')

in which X' and Z are as defined above and Y' is one of the radicals (a), (b°) or (c°) as defined above, and then, when, in the compound (I''), Y' is a radical (b°), the product thereby obtained, of formula (I''b°):

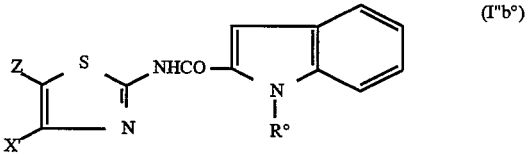 (I''b°)

is subjected, where appropriate, to an N-deprotection or to a saponification or to an acid hydrolysis;

when, in the compound (I''), Y' is a radical (c°), the product thereby obtained, of formula:

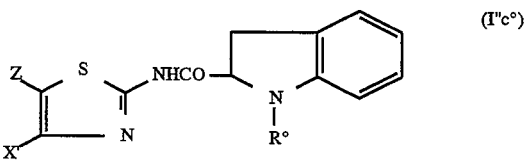 (I''c°)

is subjected to a dehydrogenation, where appropriate preceded by an N-deprotection, by a saponification or by an acid hydrolysis, to obtain a compound of formula (I') in which Y is a radical (b) wherein R is hydrogen or a group $CH_2COOR'$, Z, X' and R' being as defined above; and the product of formula (I') is isolated, as it is or in the form of one of its pharmaceutically acceptable salts or solvates.

As a functional derivative of the acid (II), it is possible to use the acid itself, where appropriate activated, its anhydride, one of its mixed anhydrides or one of its activated esters.

The condensation of the aminothiazole (III) with the acid (II) in the form of an activated ester, prepared, for example, by the action of 1-hydroxybenzotriazole on the acid in the presence of dicyclohexylcarbodiimide according to the procedure described in J. Am. Chem. Soc. 1971, 93 6318–6319, or by the action of 1-benzotriazolyloxytrisdimethylaminophosphonium hexafluorophosphate (BOP) according to the procedure described in Synthesis, 1976, 751–752, may be performed in a solvent whose nature is chosen according to the solubility of the compounds and the type of activation of the acid function, preferably in the presence of a base, for example a tertiary amine such as triethylamine; the reaction is, in general, performed at a temperature of between 0° C. and 30° C.

By the first step of the process according to the invention, a compound of formula (I") wherein Z, X' and Y' are defined as above is obtained. When, in the compound of formula (I"), Y' represents either a radical (a), or a radical (b°) in which R° is a group $CH_2COOR"$, said compound can also represent the final product of formula (I') wherein Y represents either a radical (a), or a radical (b) in which R is a group $CH_2COOR'$ in which R' is a $C_1$–$C_4$-alkyl, Z and X' being as defined above.

When, in the compound of formula (I"), Y' represents a group (b°) in which R° is an N-protecting group or a group $CH_2COOR"$, said compound can be N-deprotected to obtain compounds of formula (I') in which Y represents a group (b) wherein R is hydrogen, or alternatively it can be subjected to a saponification or to an acid hydrolysis to obtain a compound of formula (I') in which Y represents a group (b) wherein R is a $CH_2COOH$ group.

When, in the compound of formula (I"), Y' represents a group (C°), the said compound is subjected to the deprotections, to which a dehydrogenation is added.

The acids Y'COOH in which R°, in the radicals (b°) and (c°), is an acyl protecting group such as acetyl may be prepared by the action of acetyl chloride or acetic anhydride, for example, on Y'COOH in which R° is H, and in the presence of one equivalent of triethylamine or of 4-dimethylaminopyridine, for example in dichloromethane.

When the functional derivative of the acid II is a mixed anhydride, the latter may be prepared by the action of an alkyl chloroformate on the acid, in the presence of a base, generally a tertiary amine such as triethylamine; this reaction is most often performed in a solvent such as dichloromethane, dichloroethane or chloroform.

When it is desired to prepare a 2-indolecarboxamide of formula (I') where R is hydrogen, R° represents an N-protecting group in the radicals (b°) and (c°).

Thus, the derivatives (I') in which Y represents:

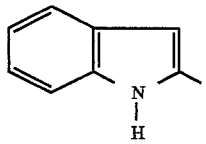

may be prepared from the compounds obtained by condensation of the aminothiazole (III) with a functional derivative of the 2-indolecarboxylic acid of formula:

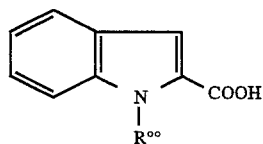

in which R°° represents an N-protecting group customarily used for the protection of the $NH_2$ groups in amino acid condensation reactions, such as: $—COOC(CH_3)_3$; $—COOCH_2C_6H_5$; $—CO—CH_3$; the N-protecting group may then be removed by standard deprotection methods.

The same compounds may also be prepared from the compounds obtained by condensation of aminothiazole (III) with 2-indolinecarboxylic acid derivatives of formula:

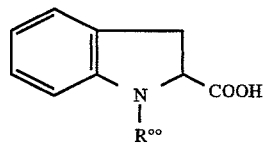

in which R°° is an N-protecting group such as $—COOC(CH_3)_3$, to obtain the compound of formula:

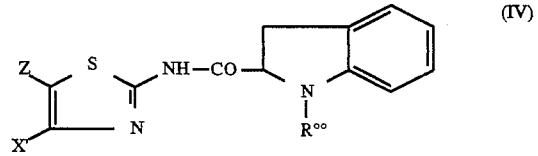

(IV)

it being possible for the group R°° to be removed from the compound (IV) by the action of a strong acid in an anhydrous medium, such as trifluoroacetic acid in dichloromethane or hydrochloric acid in ethyl ether.

The compound thereby obtained is then dehydrogenated.

The reaction is performed by the action of standard dehydrogenating reagents such as 2,3,5,6-tetrachloro-1,4-benzoquinone, 2,3-dichloro-5,6-dicyano-1,4-benzoquinone (DDQ) or cyclohexene on the indoline residue, in the presence of palladium in inert solvents having a high boiling point, such as diphenyl ether, xylene, 1,2-dimethoxyethane or 2-methoxyethyl ether, at high temperature, and preferably at the refluxing temperature of the solvent.

When the protecting group represented by R°° is acetyl, it can also constitute the group R of the substituent Y of the final product of formula (I').

The hydrolysis of the $C_1$–$C_4$-alkyl ester of the group R°, in order to obtain the products of formula (I') wherein Y represents $CH_2COOH$, is performed either in an acid medium or preferably in a basic medium, for example by the action of an inorganic base, such as an alkali metal hydroxide, in an aqueous-alcoholic medium.

The aminothiazoles 2-amino-4-(2,4,5-trimethoxyphenyl) -5-methylthiazole and 2-amino-4-(2,4,5-trimethoxyphenyl) thiazole are described in Rev. Latinoam. Quim., 1990, 21 (3–4), 102–105.

The aminothiazoles of formula:

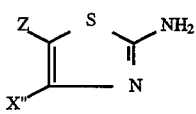

(III')

in which:

X" represents a (hetero)aryl radical chosen from 4-chloro-2,6-dimethoxyphenyl, 2,6-dimethoxy-4-methylphenyl, 4-methyl-2,3,6-trimethoxyphenyl, 2,4,6-trimethoxy-5-chlorophenyl, 2,4,6-trimethoxy-3-pyridyl, 2,4,6-trimethoxy-5-pyrimidinyl, 2,4-dimethoxy-6-methyl-3-pyridyl, 6-chloro-2,4-dimethoxy-5-pyrimidinyl, 5-chloro-2,4-dimethoxyphenyl, 5-chloro-2-methoxy-4-methylphenyl, 2,5-dimethoxy-4-methylphenyl, 4-trifluoromethyl-2,6-dimethoxyphenyl, 2,4-dimethoxy-5-methylphenyl and 5-ethyl-2,4-dimethoxyphenyl groups;

Z represents H, a $C_1$–$C_4$-alkyl or a benzyl;

with the limitation that Z represents H when X" is a phenyl radical substituted simultaneously at positions 2 and 6 or when X" is a 3-pyridyl radical substituted simultaneously at positions 2 and 4 or when X" is a 5-pyrimidinyl radical substituted simultaneously at positions 4 and 6; are new and form part of the invention.

Among the compounds of the formula (III') above, 2-amino-4-(4-chloro-2,6-dimethoxyphenyl)thiazole, 2-amino-4-(5)chloro-2,4-dimethoxyphenyl)thiazole, 2 amino-4-(5-chloro-2,4-dimethoxyphenyl)-5-methylthiazole, 2-amino-4-(5-chloro-2-methoxy-4-methylphenyl) thiazole, 2-amino-4-(2,6-dimethoxy-4-methylphenyl)thiazole, and 2-amino-4-(2,4-dimethoxy-5-methylphenyl)-5-methylthiazole, are especially preferred.

They may be prepared according to one of the processes described, in particular, in Bull. Soc. Chim. (C), 1963, 2498–2503.

Generally speaking, thiourea is reacted with an alpha-halogenated, and preferably alpha-chlorinated, ketone according to the following reaction scheme:

SCHEME 1

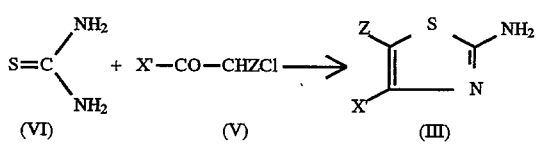

X' and Z having the same meaning as above.

The ketones (V) may be obtained, for example:

(1) by a Friedel-Crafts reaction:

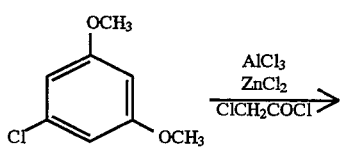

-continued

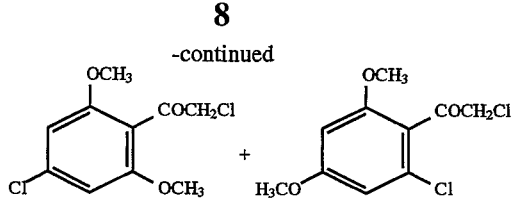

according to Chem. Pharm. Bull., 1991, 39, 9, 2400–2407;

(2) by a lithiation reaction:

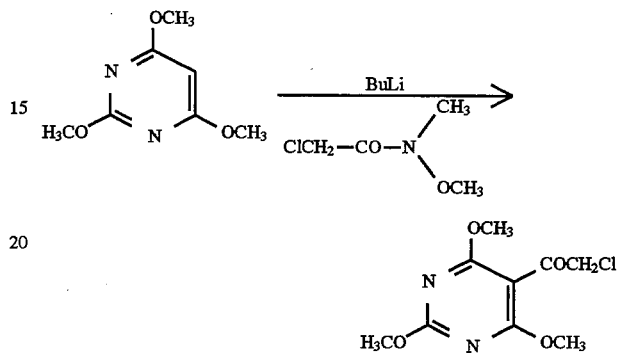

according to EP-A-0,432,040.

The aminothiazoles (III) may also be prepared in a single step using the Hoesch reaction (according to Dubois, Organic Reactions, 1949, 5, 387 or according to Satchell et al., The Chemistry of the Carbonyl Group, ed. S. Patai, Interscience, 1966, 1, 5, 233–302) on a substituted benzene derivative, followed by cyclization with thiourea.

The aminothiazoles (III) may also be prepared in one step from aromatic ketones according to the following reaction scheme:

SCHEME 2

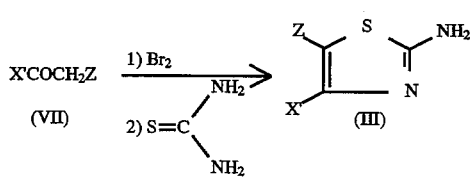

The starting aromatic ketones (VII) are prepared by a Friedel-Crafts reaction from the derivatives X'H.

The derivatives X'H are known or are prepared by known methods.

Some of the acids Y'COOH are known and are even commercially available; the others are prepared using known methods for similar molecules. They are all illustrated in EP-A-0,432,040.

Thus, the 2-indolecarboxylic acids of formula:

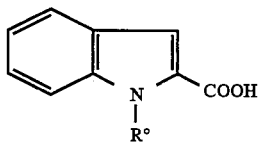

in which R° represents a $C_1$–$C_4$-alkoxycarbonylmethyl group may be prepared from commercially available 2-indolecarboxylic acids or obtained by standard processes according to SCHEME 3 below,

SCHEME 3

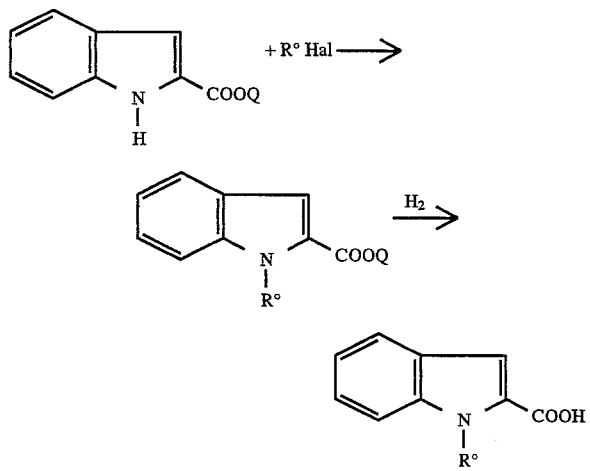

in which Hal represents a halogen atom and Q represents a benzyl group.

The starting benzyl esters of SCHEME 3 are prepared by the action of the corresponding acid on benzyl alcohol, in the presence of one of the agents for activating the acid function commonly used in peptide synthesis and as is described in EP-A-0,432,040.

The salts of the compounds of formula (I') with organic or inorganic acids or bases are prepared in the usual way by introducing the acid or base into a solution of the compound of formula (I'). The salt is isolated, depending on its solubility properties, after evaporation of the solvent or addition of a non-solvent.

The subject of the invention is also, according to another of its aspects, pharmaceutical compositions comprising the compounds (I') above.

More generally, the compounds of formula (I) have been the subject of in vitro binding studies relating to CCK receptors.

A study of the agonist effect of the compounds on amylase secretion was carried out as follows: pancreatic acini are obtained by enzymatic (collagenase) digestion of pancreas from a rat fasted for 18 hours. Aliquots (485 µl) are incubated at 37° C. for 30 minutes in the presence of increasing concentrations of agonist according to Jensen et al., J. Biol. Chem., 1982, 257 (10), 5554. Incubation is stopped by centrifugation for 15 seconds. The supernatant is kept in an ice bath to measure the amylase level according to the technique of Ceske et al., Clin. Chim. Act. 1969, 26, 437 (phadebas® reagent: amylase test commercialized by pharmacia diagnostic). The test compounds are dissolved in dimethyl sulphoxide and then in incubation buffer.

The compound of formula (I) behave as CCK-receptor agonists with $ED_{50}$ (Efficient dose inducing 50% of the amylase secretion compared to the maximal effect obtained in the presence of CCK) of the order of $10^{-9}M$.

A study of the CCK-agonist effect of the compounds on feed consumption was carried out as follows. Male Sprague-Dawley rats (200–240 g) (Charles River, France) are isolated 10 days before the experiment, and subjected every day successively to 18 hours of fasting and 6 hours of feeding: the feed is available from 10 a.m. to 4 p.m., water is available ad libitum. On the day of the experiment, the products (suspended in a methylcellulose solution at a concentration of 0.6%) or the vehicle are administered intraperitoneally. Thirty minutes after the treatment (at 10 a.m.), a known quantity of feed is introduced into the cage: feed consumption is measured 1 hour and 3 hours later.

The compounds of formula (I) decrease feed intake, and hence behave as CCK-receptor agonists (Gibbs J. et al., J. Comp. Physiol. Psychol., 1973, 84, 488–495) in particular:

N-[4-(5-chloro-2,4-dimethoxyphenyl)-2-thiazolyl]-1H-indole-2-carboxamide,

N-[4-(5-chloro-2,4-dimethoxyphenyl)-5-methyl-2-thiazolyl]-1H-indole-2-carboxamide, N-[4-(5-chloro-2,4-dimethoxyphenyl)-5-methyl-2-thiazolyl]-1-(carboxymethyl)indole-2-carboxamide trifluoroacetate, and N-[4-(5-chloro-2-methoxy-4-methylphenyl)-2-thiazolyl]-1H-indole-2-carboxamide, are active at a dose of 3 mg/kg, at which dose they reduce feed consumption by 30 to 40% relative to a control animal.

Consequently, the compounds of formula (I) are used as a CCK-receptor agonist for the preparation of medicinal products intended for combating pathologies whose treatment necessitates a stimulation by a total or partial agonist effect at the cholecystokinin receptors, and more especially for the manufacture of medicinal products intended for the treatment of certain eating disorders, obesity and diabetes, disorders of emotional, sexual and mnestic behaviour, psychoses and schizophrenia particular, Parkinson's disease and various disorders of the gastrointestinal system.

The compounds of formula (I) are of low toxicity; their toxicity is compatible with their use a medicinal product for the treatment of the disorders and complaints mentioned above.

The new compounds of formula (I') may be formulated in pharmaceutical compositions for administration to mammals, including man, for the treatment of the above-mentioned pathologies.

The dosage, which varies according to the treatment and according to the pathology in question, can range, for example, between 0.05 and 100 mg per day in adults via the oral route.

The subject of the present invention is also pharmaceutical compositions which contain one of the above compounds as active principle. These compositions are produced so as to be able to be administered via the digestive tract or parenterally.

In the pharmaceutical compositions of the present invention for oral, sublingual, subcutaneous, intramuscular, intravenous, transdermal, local or rectal administration, the active ingredient may be administered to animals and to human beings in single-dose forms of administration, mixed with traditional pharmaceutical vehicles. Suitable single-dose forms of administration comprise oral forms such as tablets, gelatin capsules, powders, granules and oral solutions or suspensions, forms for sublingual and buccal administration, forms for subcutaneous, intramuscular, intravenous, intranasal or intraocular administration and forms for rectal administration.

When a solid composition is prepared in the form of tablets, the main active ingredient is mixed with a pharmaceutical vehicle such as gelatin, starch, lactose, magnesium stearate, talc, gum arabic or the like. The tablets may be coated with sucrose or with other suitable materials, or alternatively they may be treated in such a way that they have sustained or delayed activity and release a predetermined amount of active principle continuously.

A preparation in gelatin capsules is obtained by mixing the active ingredient with a diluent and pouring the mixture obtained into soft or hard gelatin capsules.

A preparation in the form of a syrup or elixir can contain the active ingredient together with a sweetener, preferably one having negligible calorific value, methylparaben and propylparaben as an antiseptic together with a flavouring agent and a suitable colouring.

The water-dispersible powders or granules can contain the active ingredient mixed with dispersing agents or wetting agents, or suspending agents such as polyvinylpyrrolidone, as well as with sweeteners or flavour correctors.

For rectal administration, suppositories are employed, these being prepared with binding agents that melt at rectal temperature, for example cocoa butter or polyethylene glycols.

For parenteral, intranasal or intraocular administration, aqueous suspensions, isotonic saline solutions or sterile injectable solutions are used, containing pharmacologically compatible dispersing agents and/or wetting agents, for example propylene glycol or butylene glycol.

The active ingredient may also be formulated in the form of microcapsules, where appropriate with one or more vehicles or additives.

The active ingredient may also be presented in the form of a complex with a cyclodextrin, for example α-, β- or γ-cyclodextrin, 2-hydroxypropyl-β-cyclodextrin or methyl-β-cyclodextrin.

The composition can be in the form of a single dose comprising from 0.05 to 100 mg of active ingredient In what follows, examples of implementation of the invention are described, as well as processes for preparing some synthesis intermediates of formulae X'H, (V), (VII), (III) and (II). The melting points stated were determined in a capillary. The nuclear magnetic resonance spectra were recorded using tetramethylsilane as reference.

In the preparations and in the examples, the following abbreviations are used:

DCM: dichloromethane
ether: diethyl ether
iso ether: diisopropyl ether
$CCl_4$: carbon tetrachloride
MeOH; methanol
EtOH: ethanol
AcOEt: ethyl acetate
DMF: dimethylformamide
THF: tetrahydrofuran
$CHCl_3$: chloroform
$AlCl_3$: aluminium chloride
$ZnCl_2$: zinc chloride
$TiCl_4$: titanium chloride
HCl: hydrochloric acid
$H_2SO_4$: sulphuric acid
TFA: trifluoroacetic acid
$KHSO_4$: potassium hydrogen sulphate
NaOH: caustic soda
silica H: silica gel 60 H, marketed by MERCK (DARMSTADT)
tBu: tert-butyl
m.p.: melting point
b.p.: boiling point
r.t.: room temperature
NMR: nuclear magnetic resonance
s: singlet
bs: broad singlet
u.c.: unresolved complex PREPARATION I. Compounds X'H.

A) 2,4,6-Trimethoxypyrimidine

This compound is prepared according to the procedure described in J. Am. Chem. Soc., 1932, 54, 727–733.

B) 2,4-Dimethoxy-6-methylpyridine

First, 1,2-dihydro-4-hydroxy-6-methyl-2-oxopyridine is prepared according to the procedure described in J. Heterocycl. Chem., 1975, 12 (5), 963–967.

A mixture of 7.51 g of the compound obtained above and 75 ml of phosphorus oxychloride is heated to 120° C. for 2 hours 30 minutes. The reaction mixture is left overnight at r.t. and evaporated under vacuum, the residue is taken up in ice, saturated sodium hydrogen carbonate solution is added to pH 10, the mixture is extracted with ether, the organic phase is dried over sodium sulphate and the solvent is evaporated off under vacuum. 9.7 g of 2,4-dichloro-6-methylpyridine are obtained in the form of an oil.

A mixture of 9.7 g of the compound obtained above and 7.13 g of sodium methylate in 15 ml of MeOH is heated for 36 hours to a temperature of between 130° and 140° C. in a reactor under a pressure of 5 bars. After cooling, 200 ml of ether are added, the mixture is filtered and the filtrate is evaporated under vacuum. The residue is chromatographed on silica, eluting with DCM. 4 g of the monomethoxy product are obtained, which product is reacted again. A mixture of 4 g of the above product with a solution of sodium methylate prepared from 0.7 g of sodium and 15 ml of MeOH is heated for 20 hours to a temperature of between 132° and 140° C. in a reactor under a pressure of 5 bars. After cooling, 200 ml of ether are added, the mixture is filtered and the filtrate is evaporated at atmospheric pressure. The residue is distilled under vacuum, and 2.5 g of the expected product, b.p.=101°–103° C. at 0.02 bar, are obtained.

C) 1-Chloro-2,4-dimethoxybenzene.

82.6 g of a solution containing 50% by weight of cesium hydroxide in water are added to a solution of 20 g of 4-chlororesorcinol in 200 ml of EtOH. The mixture is evaporated under vacuum, the residue is taken up in isopropanol, the organic phase is evaporated again and this operation is repeated three times. The cesium salt thereby obtained is dissolved in 100 ml of DMF. 40 ml of methyl iodide are added and the reaction mixture is heated to 80° C. for 3 hours. It is evaporated under vacuum, the residue is taken up with DCM, the organic phase is washed with saturated sodium hydrogen carbonate solution and dried over magnesium sulphate and the solvent is evaporated off under vacuum. The residue is chromatographed on silica, eluting with toluene. The eluate is distilled under vacuum, and 13 g of the expected product, b.p.=138° C. at 0.02 bar pressure, are obtained.

D) 2-Chloro-5-methoxytoluene 42.05 g of a solution containing 50% by weight of cesium hydroxide in water are added to a solution of 20 g of 4-chloro-3-methylphenol in 200 ml of EtOH. The solvent is evaporated off under vacuum, the residue is taken up in isopropanol, the organic phase is evaporated again under vacuum and this operation is repeated three times. The caesium salt thereby obtained is dissolved in 100 ml of DMF. 30 ml of methyl iodide are added and the reaction mixture is heated to 80° C. for 3 hours. It is evaporated under vacuum, the residue is taken up with DCM, the organic phase is washed with water and with saturated sodium carbonate solution and dried over magnesium sulphate and the solvent is evaporated off under vacuum. The residue is chromatographed on silica, eluting with toluene. The eluate is distilled under vacuum, and 14 g of the expected product, b.p.=105° C. under 0.02 bar pressure, are obtained.

E) 2,5-Dimethoxytoluene

A mixture of 12 g of methylhydroquinone, 45 g of potassium carbonate and 45 g of dimethyl sulphate in 300 ml of anhydrous acetone is heated to reflux for 4 days. After cooling, the reaction mixture is filtered and the filtrate is evaporated under vacuum. The residue is taken up in 150 ml of concentrated aqueous ammonia, the mixture is left stirring for 2 hours, diluted with water and extracted with DCM, the organic phase is dried over magnesium sulphate and the solvent is evaporated off under vacuum. The residue is chromatographed on silica H, eluting with a heptane/DCM (50:50; v/v) mixture. 12 g of the expected product are obtained.

NMR spectrum at 200 MHz in DMSO: 2.05 ppm:s:3H; 3.60 ppm:s:3H; 3.65 ppm:s:3H; 6.5 to 6.9 ppm:u.c.:3H.

PREPARATION II. alpha-Chloroketones of formula (V).

A) 1-(2,6-Dimethoxy-4-methylphenyl)-2-chloro-1-ethanone 7.61 g of 3,5-dimethoxytoluene and 6.10 g of tetramethylethylenediamine are dissolved under nitrogen in 150 ml of hexane. The solution is cooled to 0° C., 32.8 ml of 1.6 M butyllithium in hexane are added and the mixture is stirred at 10° C. for 20 minutes and then at 20° C. for 1 hour. To the lithium derivative cooled to −10° C., a solution, cooled to 0° C., of 6.13 g of N-methoxy-N-methylchloroacetamide in 50 ml of THF is added in the course of 20 minutes. The reaction mixture is left for one hour at a temperature of between 0° and 5° C. and for one hour at 20° C., and then poured into 100 ml of water. The resulting mixture is extracted with twice 300 ml of diethyl ether, the ether phases are washed with saturated sodium chloride solution, and the organic phases are dried over magnesium sulphate, filtered and concentrated under vacuum. The residue is chromatographed on silica, eluting with a DCM/hexane (50:50; v/v) mixture. Concentration of the pure fractions yields 1.6 g of the expected product; m.p. 82°–84° C.

B) 1-(2,4,6-Trimethoxy-3-pyridyl)-2-chloro-1-ethanone (according to Chem. Pharm. Bull., 1986, 34 3658 and J. Am. Chem. Soc., 1932, 54 727)

24 g of 2,6-dichloropyridine, 200 ml of trifluoroacetic acid and 28 ml of 33% hydrogen peroxide are heated to 100° C. for 4 hours. The mixture is cooled, 600 ml of water are then added and the resulting mixture is concentrated under vacuum to a volume of 50–100 ml. It is alkalinized with sodium hydrogen carbonate and then extracted with DCM, and the organic phase is separated after settling has taken place and dried over sodium sulphate. It is filtered and concentrated under vacuum, and the residue is recrystallized from AcOEt to obtain 18.8 g of 2,6-dichloropyridine N-oxide; m.p.=138°–140° C.

18.8 g of the compound prepared above are heated to reflux for 6 hours in 40 ml of phosphorus oxychloride and left overnight at r.t., and the mixture is then concentrated under vacuum. The residue is poured into cold water and then, successively, the mixture is neutralized with sodium carbonate and extracted with ether, and the ether phase is separated after settling has taken place, dried over sodium sulphate, filtered and concentrated under vacuum. The residue is chromatographed on silica gel, eluting with a DCM/heptane (60:40; v/v) mixture. Concentration of the pure fractions yields 14.6 g of 2,4,6-trichloropyridine.

A mixture of 14.6 g of the product prepared above and 129.7 g of sodium methylate in 400 ml of MeOH is heated to reflux overnight. 0.7 liter of water is added and then, successively, the mixture is extracted with DCM and the organic extract is washed with water and dried over sodium sulphate. It is concentrated under vacuum, and the residue is recrystallized from pentane to yield 9.5 g of 2,4,6-trimethoxypyridine; m.p.=47°–49° C.

7.5 ml of 1.6 M methyllithium in ether and 0.02 ml of diisopropylamine are added under nitrogen to 15 ml of anhydrous THF at −40° C., the mixture is then stirred for 5 minutes, and 1.13 g of the pyridine derivative prepared above, dissolved in 10 ml of THF, are added at −40° C. in the course of 10 minutes. The mixture is stirred for 3 hours at 0° C. It is then cooled to −70° C., 0.824 g of N-methyl-N-methoxychloroacetamide, dissolved in 20 ml of THF, is added in the course of 5 minutes, and the temperature is allowed to rise to 10° C. in the course of one hour. The reaction mixture is poured into 300 ml of cold water saturated with sodium chloride, and is extracted with ether. The organic extract is successively washed with saturated sodium chloride solution and separated after settling has taken place, dried over sodium sulphate, filtered and concentrated under vacuum. The residue is chromatographed on silica gel, eluting with a cyclohexane/AcOEt (80:20; v/v) mixture. Concentration of the fractions of pure product yields 0.61 g of the expected ethanone; m.p.=85°–87° C.

C) 1-(2,4-Dimethoxy-5-methylphenyl)-2-chloro-1-ethanone

This compound is prepared according to Chem. Pharm. Bull., 1991, 39 (9), 2400–2407.

A suspension of 5.24 g of AlCl$_3$ and 0.52 g of ZnCl$_2$ in 40 ml of 1,2-dichloroethane is cooled to 0° C., and a solution of 5.0 g of 2,4-dimethoxytoluene in 20 ml of 1,2-dichloroethane is added dropwise. The mixture is then cooled to −10° C., and a solution of 2.9 ml of chloroacetyl chloride in 1.5 ml of 1,2-dichloroethane is added dropwise while the temperature of the reaction medium is maintained at between −10° C. and −7° C. The mixture is left stirring while the temperature is allowed to rise to r.t., the reaction medium is poured into a mixture of ice and concentrated HCl, the resulting mixture is extracted with DCM, the combined organic phases are washed with water and dried over magnesium sulphate and the solvents are evaporated off under vacuum. The residue is taken up in heptane and the precipitate formed is filtered off. 3.0 g of the expected product, m.p.=166°–167° C., are obtained.

D) 1-(4-Trifluoromethyl-2,6-dimethoxyphenyl)-2-chloro-1-ethanone

A solution of 9.73 g of 3-amino-5-methoxy-1-trifluoromethylbenzene in 400 ml of 2N HCl is cooled to 10° C., and a solution of 3.80 g of sodium nitrite in 20 ml of water is added in the course of 10 minutes. The mixture is left stirring for 30 minutes at 10° C., and a solution of 800 ml of concentrated H$_2$SO$_4$ in 800 ml of water is added while the temperature is maintained below 20° C. The mixture is then heated to 95° C. for 2 hours and left overnight at r.t. 1000 g of ice are added to the reaction medium, the mixture is extracted with ether, the organic phase is washed with saturated sodium chloride solution and dried over sodium sulphate and the solvent is evaporated off under vacuum. 9.8 g of 3-hydroxy-5-methoxy-1-trifluoromethylbenzene, m.p.≈75° C. (according to J. Chem. Soc., 1951, 2013) are obtained.

7.90 g of K$_2$CO$_3$ are added to a solution of 9.8 g of the compound prepared above in 100 ml of acetone, and the mixture is heated to 50° C. 6.74 g of dimethyl sulphate are then added dropwise and in the course of 20 minutes at this temperature, and the mixture is heated to reflux for 2 hours. The reaction mixture is evaporated under vacuum, the residue is taken up with 30 ml of 20% aqueous ammonia solution and with 50 ml of water, the mixture is extracted with ether, the organic phase is washed with saturated sodium chloride solution and dried over sodium sulphate and the solvent is evaporated off under vacuum. 8.7 g of 3,5-dimethoxy-1-trifluoromethylbenzene are obtained after distillation under vacuum, b.p.=92°–94° C. at 0.02 bar pressure.

5.09 g of tetramethylethylenediamine are added to a solution of 8.6 g of the compound prepared above in 100 ml of hexane. The mixture is cooled to −5° C., 27.4 ml of a 1.6 M solution of butyllithium in hexane are added under a nitrogen atmosphere in the course of 15 minutes, and the resulting mixture is then left stirring for 1 hour 30 minutes at a temperature of between −5° C. and +5° C. The solution of lithium derivative is then added to a solution, cooled to −25° C., of 5.41 g of N-methoxy-N-methylchloroacetamide in 45 ml of THF, and the mixture is left stirring for 2 hours while the temperature is allowed to rise to +5° C. 100 ml of water are added; the mixture is extracted with ether, the organic phase is washed with saturated sodium chloride solution and dried over sodium sulphate and the solvent is evaporated off under vacuum. 3.6 g of the expected product are obtained after crystallization in hexane, m.p.=120°–122° C.

The chlorinated ketones of formula (V) described in TABLE I were prepared according to one of the processes employed above and using the appropriate starting materials.

TABLE I

| X'CO—CH$_2$Cl (V) X' | m.p.; °C. |
|---|---|
| ![structure: benzene with OCH$_3$, OCH$_3$, Cl] | |
| ![structure: pyrimidine with OCH$_3$, OCH$_3$, H$_3$CO, N, N] | 90–92 |
| ![structure: pyrimidine with Cl, OCH$_3$, H$_3$CO, N, N] | 96–98 |
| ![structure: pyridine with OCH$_3$, OCH$_3$, H$_3$C, N] | 84–86 |

PREPARATION III. Aromatic ketones of formula (VII)

A) 1-(5-Chloro-2,4-dimethoxyphenyl)-1-ethanone

A mixture of 2 g of 1-chloro-2,4-dimethoxybenzene and 0.9 g of acetyl chloride in 20 ml of CCl$_4$ is cooled to 0° C., and a solution of 1.3 ml of TiCl$_4$ in 7 ml of CCl$_4$ is added dropwise. The reaction mixture is left stirring for 2 hours while the temperature is allowed to rise to r.t. It is poured into a mixture of concentrated HCl and ice, the resulting mixture is extracted with DCM, the organic phase is dried over magnesium sulphate and the solvents are evaporated off under vacuum. The residue is chromatographed on silica H, eluting with a DCM/heptane (70:30; v/v) mixture. 1.19 g of the expected product, m.p.=138° C., are obtained.

B) 1-(5-Chloro-2,4-dimethoxyphenyl)-1-propanone

A mixture of 2.01 g of 1-chloro-2,4-dimethoxybenzene and 1.08 g of propionyl chloride in 20 ml of CCl$_4$ is cooled to 0° C., and a solution of 1.3 ml of TiCl$_4$ in 7 ml of CCl$_4$ is added dropwise. The reaction mixture is left stirring for 2 hours while the temperature is allowed to rise to r.t. It is poured into a mixture of concentrated HCl and ice, the resulting mixture is extracted with DCM, the organic phase is dried over magnesium sulphate and the solvents are evaporated off under vacuum. The residue is chromatographed on silica H, eluting with a DCM/heptane (80:20; v/v) mixture. 1.14 g of expected product, m.p.=115° C., are obtained.

C) 1-(5-Chloro-2-methoxy-4-methylphenyl)-1-ethanone

A suspension of 2.12 g of AlCl$_3$ in 20 ml of CCl$_4$ is cooled to 0° C. under a nitrogen atmosphere, and a solution of 1.25 g of acetyl chloride in 10 ml of CCl$_4$ is added dropwise. A solution of 2.5 g of 2-chloro-5-methoxytoluene in 10 ml of CCl$_4$ is then added dropwise, and the mixture is left stirring for 2 hours while the temperature is allowed to rise to r.t. The mixture is poured into a mixture of concentrated HCl and ice, the resulting mixture is extracted with DCM, the organic phase is dried over magnesium sulphate and the solvent is evaporated off under vacuum. The residue is chromatographed on silica H, eluting with a DCM/heptane (70:30; v/v) mixture. 0.68 g of the expected product, m.p.=83° C., is obtained.

D) 1-(5-Chloro-2-methoxy-4-methylphenyl)-1-propanone

A suspension of 2.55 g of AlCl$_3$ in 30 ml of DCM is cooled to 0° C. under a nitrogen atmosphere, and a solution of 1.77 g of propionyl chloride in 15 ml of DCM is added dropwise. A solution of 3 g of 2-chloro-5-methoxytoluene in 15 ml of DCM is then added dropwise, and the reaction mixture is left stirring for 2 hours. It is poured into a mixture of concentrated HCl and ice, the organic phase is extracted with DCM and dried over magnesium sulphate and the solvent is evaporated off under vacuum. The residue is chromatographed on silica, eluting with a DCM/heptane (70:30; v/v) mixture. 2.2 g of the expected product, m.p.= 79° C., are obtained.

E) 1-(5-Ethyl-2,4-dimethoxyphenyl)-1-propanone

A suspension of 10 g of 4-ethylresorcinol in 20 ml of boron trifluoride etherate is cooled to +4° C., and 11.7 g of propionic anhydride are added dropwise. The reaction mixture is heated to 75° C. for 6 hours and poured, after cooling, into a mixture of water and ice. The resulting mixture is left stirring for 2 hours, the precipitate formed is filtered off, washed with water and taken up in AcOEt, the organic phase is washed with water and dried over sodium sulphate and the solvent is evaporated off under vacuum. The residue is chromatographed on silica, eluting with DCM and then with a DCM/AcOEt (90:10; v/v) mixture. 9.32 g of 1-(5-ethyl-2,4-dihydroxyphenyl)-1-propanone, m.p.=74°–75° C., are obtained.

A suspension of 5 g of the compound prepared above, 30 g of potassium carbonate and 30 ml of dimethyl sulphate in 500 ml of acetone is heated to reflux for 48 hours. After cooling, some insoluble matter is filtered off, the filtrate is evaporated under vacuum and the residue is taken up in 100 ml of concentrated aqueous ammonia. After 1 hour of stirring, 400 ml of water are added, the precipitate formed is filtered off, washed with water and taken up in DCM, the organic phase is washed with water and dried over magnesium sulphate and the solvent is evaporated off under vacuum. 5.68 g of the expected product, m.p.=64°–65° C., are obtained.

F) 1-(2,4-Dimethoxyphenyl)-3-phenyl-1-propanone

A solution of 45.5 g of 3-phenylpropanoyl chloride in 50 ml of $CCl_4$ is added dropwise to a suspension of 43.2 g of $AlCl_3$ and 37.5 g of 1,3-dimethoxybenzene in 210 ml of $CCl_4$. The reaction mixture is left stirring for 1 hour at r.t. and poured into a mixture of 400 g of ice and 150 ml of concentrated HCl. After 30 minutes of stirring, the resulting mixture is extracted with DCM, the combined organic phases are washed with saturated sodium hydrogen carbonate solution and dried over sodium sulphate and the solvents are evaporated off under vacuum. 66.5 g of oil of the expected product are obtained, which oil is used as it is.

The aromatic ketones of formula (VII) described in TABLE II are prepared according to one of the processes employed above and using the appropriate starting materials.

TABLE II

| X'COCH$_2$Z (VII) | | |
|---|---|---|
| X' | Z | m.p.; °C. |
| H$_3$CO—⟨benzene ring with H$_3$C, OCH$_3$⟩ | —H | 78 |
| H$_3$CO—⟨benzene ring with H$_3$C, OCH$_3$⟩ | —CH$_3$ | 77 |
| H$_3$C—⟨benzene ring with H$_3$CO, OCH$_3$⟩ | —CH$_3$ | 78 |
| ⟨benzene ring with H$_3$CO, OCH$_3$⟩ | —CH$_2$CH$_2$CH$_3$ | b.p. = 120° C. at 1.33 × 10$^{-5}$ bar |
| H$_3$CO—⟨benzene ring with H$_3$CO, OCH$_3$⟩ | —CH$_3$ | 100 |

PREPARATION IV. 2-Aminothiazoles of formula (III)

A) 1-Amino-4-(2,6-dimethoxy-4-methylphenyl)thiazole 0.41 g of the product prepared above according to PREPARATION II.A and 0.164 g of thiourea are dissolved in 50 ml of absolute EtOH. The reaction mixture is heated to reflux for 18 hours and then concentrated under vacuum. The residue is taken up in 100 ml of 2N NaOH solution, the mixture is then extracted with twice 200 ml of DCM, and the organic phases are separated after settling has taken place, dried over sodium sulphate, filtered and concentrated under vacuum. The residue crystallizes in ether to yield 0.34 g of the expected aminothiazole; m.p.=204°–206° C.

B) 2-Amino-4-(2,4,6-trimethoxy-3-pyridyl)thiazole

A mixture of 0.55 g of ketone obtained according to PREPARATION II.B and 0.21 g of thiourea in 25 ml of absolute EtOH is heated to reflux for 24 hours. The reaction mixture is concentrated under vacuum, the residue is taken up in water and 10% sodium carbonate solution is added. The mixture is extracted with AcOEt, and the organic phase is dried over sodium sulphate, filtered and concentrated under vacuum. The residue crystallizes in a minimum of iso ether. 0.51 g of the expected thiazole, m.p.=191° C., is obtained.

C) 2-Amino-4-(5-chloro-2,4-dimethoxyphenyl)thiazole

A solution of 0.26 ml of bromine in 10 ml of $CCl_4$ is added dropwise at r.t. to a solution of 1.08 g of the compound obtained in PREPARATION III.A in 20 ml of $CCl_4$. The organic phase is washed with water and dried over magnesium sulphate and the solvent is evaporated off under vacuum. The residue is taken up in 20 ml of EtOH, 2 g of thiourea are added, and the mixture is heated to reflux for 3 hours. It is evaporated under vacuum, the residue is extracted with DCM, and the organic phase is washed with saturated sodium carbonate solution, dried over magnesium sulphate and evaporated under vacuum. The residue is chromatographed on silica, eluting with a DCM/MeOH (100:1; v/v) mixture. 0.92 g of the expected product, m.p.= 162° C., is obtained.

D) 2-Amino-4-(5-chloro-2,4-dimethoxyphenyl)-5-methylthiazole

A solution of 0.25 ml of bromine in 5 ml of DCM is added dropwise at r.t. to a solution of 1.12 g of the compound obtained in PREPARATION III.B in 20 ml of DCM. The organic phase is washed with water and dried over magnesium sulphate and the solvent is evaporated off under vacuum. The residue is taken up in 20 ml of EtOH, 1.0 g of thiourea is added and the mixture is heated to reflux for 2 hours. It is evaporated under vacuum, the residue is taken up with saturated sodium carbonate solution, the mixture is extracted with DCM, and the organic phase is dried over magnesium sulphate and evaporated under vacuum. The residue is taken up in ether and the precipitate formed is filtered off. 1.26 g of the expected product, m.p.=188° C., are obtained.

The 2-aminothiazoles of formula (III) described in TABLE III below were synthesized by applying the above processes.

TABLE III
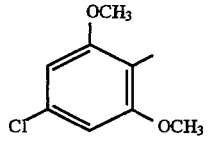
(III)
| X' | Z | m.p.; °C. or NMR salt where appropriate |
|---|---|---|
| 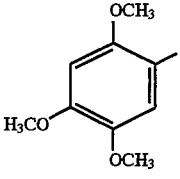 | H | 194–195 |
| 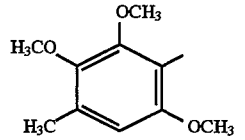 | H | 176 |
| 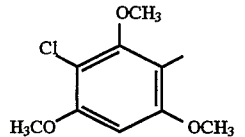 | H | (200 MHz, DMSO): 2.21(s, 3H); 3.60(s, 3H); 3.68(s, 3H); 3.75(s, 3H); 6.30(s, 1H); 6.61(s, 1H); 6.80(bs, 2H). |
| 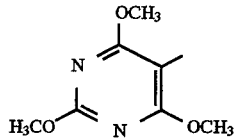 | H | (200 MHz, DMSO): 3.57(s, 3H); 3.80(s, 3H); 3.86(s, 3H); 6.65(s, 1H); 6.80(s, 1H); 9.1(bs, 2H); 13(bs, 1H). Hydrobromide |
| 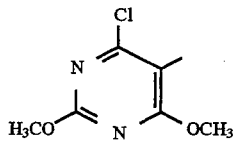 | H | 209–211 |
| 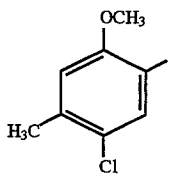 | H | 223–225 |
| 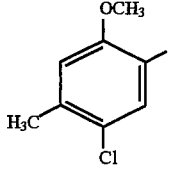 | H | 178 |
|  | CH$_3$ | 116 |

TABLE III-continued
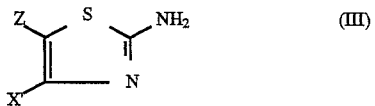 (III)
| X' | Z | m.p.; °C. or NMR salt where appropriate |
|---|---|---|
| 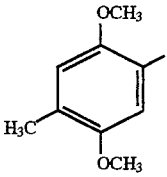 | H | (200 MHz, DMSO): 2.22(s, 3H); 3.8(s, 3H); 3.9(s, 3H); 6.8 to 7.7(u.c. 2H + 3H). |
| 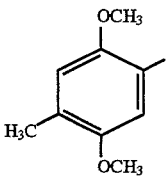 | CH₃ | 138 |
| 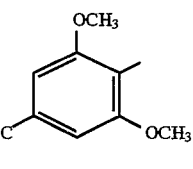 | H | 200–202 |
| 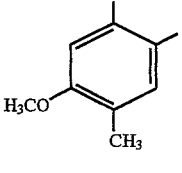 | H | 138–139 |
| 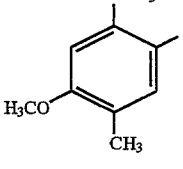 | CH₃ | 184 |
| 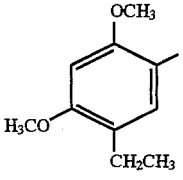 | CH₃ | 124–125 |
| 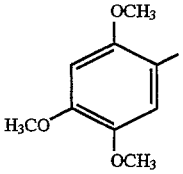 | CH₃ | (200 MHz, DMSO): 1.97(s, 3H); 3.60(s, 3H); 3.63(s, 3H); 3.72(s, 3H); 6.58(bs, 2H); 6.60(s, 1H); 6.77(s, 1H). |
| 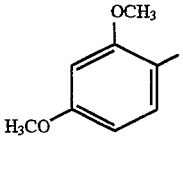 |  | 202–203 |

TABLE III-continued

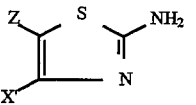

| X' | Z | m.p.; °C. or NMR salt where appropriate |
|---|---|---|
| 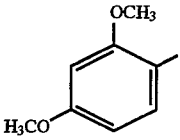 | CH₂CH₂CH₃ | 120–121 |

PREPARATION V. Indolecarboxylic acids (II)

The indolecarboxylic acids are prepared according to EP-A-0,432,040.

EXAMPLE 1

N-[4-(2,6-Dimethoxy-4-methylphenyl)-2-thiazolyl]-1H-indole-2-carboxamide hydrochloride monohydrate (method A)

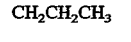

0.33 g of the amine obtained above according to PREPARATION IV.A, 0.29 g of N-acetyl-2-indolecarboxylic acid, 0.7 g of BOP and 0.16 g of triethylamine are dissolved in 40 ml of DCM. The reaction mixture is stirred for 48 hours at r.t. and, successively, 50 ml of a pH 2 buffer solution are added, and the organic phase is separated after settling has taken place, dried over sodium sulphate, filtered and concentrated under vacuum. The residue is taken up in 80 ml of 96° strength EtOH, 10 ml of 2N NaOH solution are added and the reaction mixture is stirred at r.t. for 2 and a half hours. The solution is neutralized with 1.8 ml of concentrated HCl. The precipitate formed is separated by filtration, washed with water and dried under vacuum at 60° C. to yield 0.45 g of the expected compound, m.p.=250°–252° C.

EXAMPLE 2

N-[4-(2,4,6-Trimethoxy-3-pyridyl)-2-thiazolyl]-1H-indole-2-carboxamide (method A).

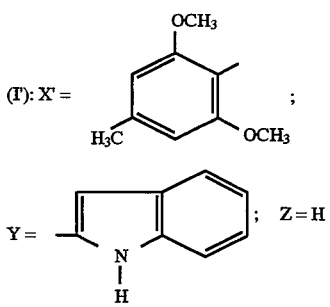

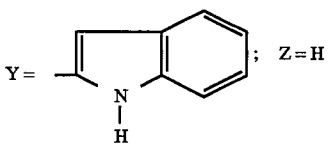

A solution of 25 ml of DCM, 0.5 g of aminothiazole obtained according to PREPARATION IV.B, 0.40 g of N-acetyl-2-indolecarboxylic acid, 0.99 g of BOP and 0.23 g of triethylamine is stirred for 24 hours at r.t. 20 ml of water are added, and the organic phase is separated after settling has taken place, dried over sodium sulphate, filtered and concentrated under vacuum. The residue is chromatographed on silica gel H, eluting with DCM/MeOH (100:1; v/v). A front impurity is removed, and the coupling product corresponding to the derivative acetylated on the indole nitrogen is then eluted. These fractions are concentrated under vacuum and the residue is dissolved in 50 ml of absolute EtOH. 5 ml of 2N NaOH solution are added to this solution, and the reaction mixture is stirred at r.t. for 1 H 30 min. It is neutralized by adding 0.85 ml of concentrated HCl and concentrated under vacuum. The residue is taken up in water to which sodium carbonate is added, and the precipitate is filtered off and washed successively with water and then with absolute EtOH to obtain 0.44 g of the expected product, m.p.=285°–287° C.

EXAMPLE 3

N-[4-(2,6-Dimethoxy-4-methylphenyl)-2-thiazolyl]-quinoline-3-carboxamide (method B).

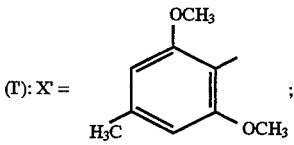

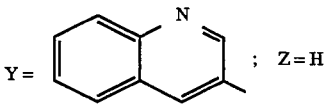

1 g of 2-amino-4-(2,6-dimethoxy-4-methylphenyl)-thiazole, 0.76 g of 3-quinolinecarboxylic acid, 0.65 ml of triethylamine and 2.15 g of BOP are dissolved in 10 ml of DMF, and the reaction mixture is left at r.t. for 48 hours. It is then poured into pH 2 buffer solution, a precipitate is separated by filtration, and the yellow solid is successively washed with water, stirred in 5% sodium carbonate solution, filtered off and thereafter dissolved in DCM. The solution is washed with 5% sodium carbonate solution and then, successively, the organic phase is separated after settling has taken place, dried over magnesium sulphate, filtered and concentrated under vacuum. The residue is stirred in ether, filtered off and dried to yield 1.58 g of the expected compound, m.p.=245°246° C.

EXAMPLE 4

N-[4-(4-Chloro-2,6-dimethoxyphenyl)-2-thiazolyl]-1-(carboxymethyl)indole-2-carboxamide (method C).

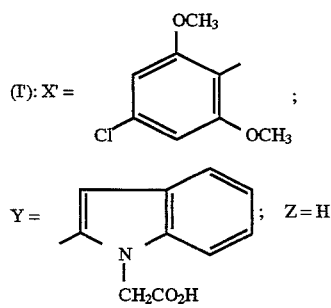

0.7 g of 2-amino-4-(2,6-dimethoxy-4-chlorophenyl) thiazole, 0.61 g of N-(methoxycarbonylmethyl)-2-indolecarboxylic acid, 0.42 ml of triethylamine and 1.4 g of BOP are dissolved in 5 ml of DMF, and the reaction mixture is then left for 48 hours at r.t. The mixture is poured into pH 2 sulphate buffer, and the precipitate is then filtered off and thereafter washed with water and dissolved in DCM. The solution is washed with 5% sodium hydrogen carbonate solution and then with pH 2 sulphate buffer, and the organic phase is separated after settling has taken place, dried over sodium sulphate, filtered and concentrated under vacuum. The residue is chromatographed on silica gel H. Concentration of the fractions of pure product yields 1.08 g of the expected methyl ester; m.p.=236°–237° C.

1.08 g of the methyl ester prepared above are dissolved in 100 ml of 95° strength EtOH in the presence of 1.5 ml of 2N NaOH. The reaction mixture is stirred at r.t. for 48 hours and concentrated under vacuum. The residue is taken up in water, and concentrated HCl is then added dropwise to pH 1. The precipitate is filtered off and dried to obtain 0.84 g of the expected hydrochloride; m.p.>300° C.

EXAMPLE 5

N-[4-(2,6-Dimethoxy-4-methylphenyl)-2-thiazolyl]-1-(carboxymethyl)indole-2-carboxamide trifluoroacetate (method D).

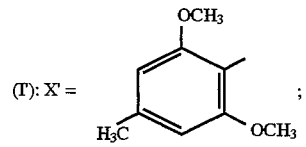

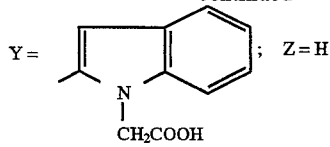

1.07 g of N-[4-(2,6-dimethoxy-4-methylphenyl)-2-thiazolyl]-1-(tert-butoxycarbonylmethyl)indole-2-carboxamide (prepared according to EP-A-0,432,040) are dissolved in a mixture of 2 ml of anisole and 20 ml of TFA. The reaction mixture is left for ¾ hour at r.t. and then concentrated under vacuum. The residue is taken up in ether, and the precipitate is then filtered off and dried in an oven to obtain 1.13 g of the expected compound; m.p.=223°–224° C.

EXAMPLE 6

N-[4-(2,3,6-Trimethoxy-4-methylphenyl)-2-thiazolyl]-1H-indole-2-carboxamide (method E).

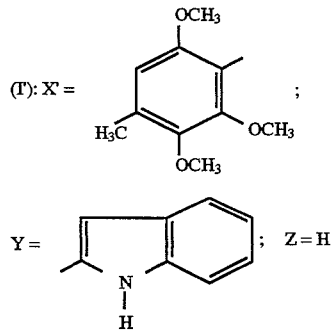

0.16 g of 2-amino-4-(2,3,6-trimethoxy-4-methylphenyl) thiazole is dissolved in 10 ml of DMF. 0.18 g of N-(tert-butyloxycarbonylmethyl)-2-indolinecarboxylic acid, 0.2 ml of triethylamine and 0.38 g of BOP are added, and the reaction mixture is left stirring for 48 hours. 100 ml of water are added, the resulting mixture is extracted with AcOEt, and the organic phase is separated after settling has taken place, dried over sodium sulphate and concentrated under vacuum. The residue is dissolved in 10 ml of CHCl₃, 10 ml of TFA are then added and the reaction mixture is stirred at r.t. for 2 hours 30 minutes. It is concentrated under vacuum, adding three times 20 ml of benzene. The residue is dissolved in 20 ml of dimethoxyethane, 0.1 ml of triethylamine and 0.112 g of DDQ are then added and the reaction mixture is left overnight at room temperature. It is concentrated under vacuum, and the residue is taken up in AcOEt and washed successively with 1N NaOH solution, with KHSO₄ solution and with sodium chloride solution; the organic phase is separated after settling has taken place, dried over sodium sulphate, filtered and concentrated under vacuum. The residue is chromatographed on silica gel, eluting with CHCl₃/AcOEt (50:50; v/v). The fractions of pure products are concentrated under vacuum, and the residue is solidified in pentane to yield 0.08 g of the expected product; m.p.= 200° C.

EXAMPLE 7

N-[4-(4-Chloro-2,4-dimethoxyphenyl)-2-thiazolyl]-1H-indole-2-carboxamide (method F).

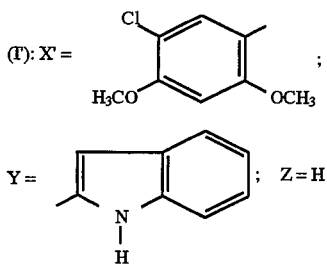

A mixture of 0.9 g of the compound obtained in PREPARATION IV.C, 0.67 g of N-acetyl-2-indolecarboxylic acid, 1.5 g of BOP and 0.46 ml of triethylamine in 4 ml of DMF is stirred at r.t. overnight. The reaction mixture is poured into pH 2 buffer solution, and the precipitate formed is filtered off and washed with water. The precipitate is taken up with DCM, and the organic phase is washed with saturated sodium hydrogen carbonate solution, dried over magnesium sulphate and evaporated under vacuum. The residue is chromatographed on silica, eluting with a DCM/AcOEt (100:1; v/v) mixture. The derivative acetylated on the indole nitrogen which is obtained is taken up in 30 ml of EtOH, 1 g of sodium carbonate is added and the reaction mixture is stirred overnight at r.t. It is evaporated under vacuum, the residue is taken up in water, and the precipitate formed is filtered off, washed with water and dried under vacuum in an oven. 0.56 g of the expected product, m.p.=293° C., is obtained.

EXAMPLE 8

N-[4-(5-Chloro-2,4-dimethoxyphenyl)-5-methyl-2-thiazolyl]-1-H-indole-2-carboxamide (method F).

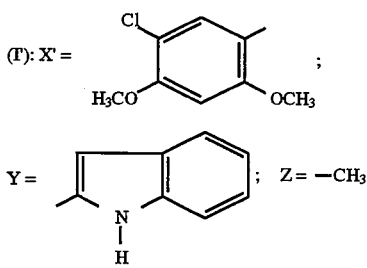

A mixture of 1.24 g of the compound obtained in PREPARATION IV.D, 0.88 g of N-acetyl-2-indolecarboxylic acid, 1.95 g of BOP and 0.60 ml of triethylamine in 4 ml of DMF is stirred at r.t. overnight. The reaction mixture is poured into pH 2 buffer solution, and the precipitate formed is filtered off and washed with water. The precipitate is taken up with DCM, and the organic phase is washed with saturated sodium hydrogen carbonate solution, dried over magnesium sulphate and evaporated under vacuum. The residue is chromatographed on silica, eluting with a DCM/AcOEt (100:1; v/v) mixture. The derivative acetylated on the indole nitrogen which is obtained is taken up in 30 ml of EtOH, 2 g of sodium carbonate are added and the reaction mixture is stirred overnight at r.t. It is evaporated under vacuum, the residue is taken up in water, and the precipitate formed is filtered off washed with water and then with ether and dried under vacuum in an oven. 0.81 g of the expected product, m.p.=249° C., is obtained.

EXAMPLE 9

N-[4-(5-Chloro-2,4-dimethoxyphenyl)-5-methyl-2-thiazolyl]-1-(carboxymethyl)indole-2-carboxamide trifluoroacetate (method G).

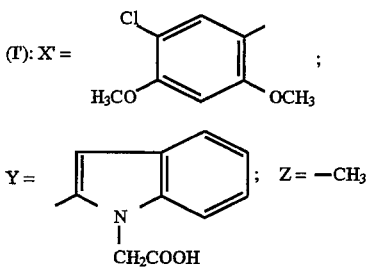

A mixture of 1 g of the compound obtained in PREPARATION IV.D, 0.96 g of N-(tert-butoxycarbonylmethyl)-2-indolecarboxylic acid, 1.6 g of BOP and 0.49 ml of triethylamine in 6 ml of DMF is stirred at r.t. overnight. The reaction mixture is poured into pH 2 buffer solution, and the precipitate formed is filtered off and washed with water. The precipitate is taken up with DCM, and the organic phase is washed with pH 2 buffer solution and with saturated sodium hydrogen carbonate solution, dried over magnesium sulphate and evaporated under vacuum. The residue is chromatographed on silica, eluting with a DCM/MeOH (100:1.5; v/v) mixture. The tert-butyl ester obtained is taken up in 10 ml of TFA and left stirring for 1 hour 30 minutes at r.t. The mixture is evaporated under vacuum, the residue is taken up in water, and the precipitate formed is filtered off, washed with water and dried under vacuum in an oven. 1.37 g of the expected product, m.p. 167° C., are obtained.

EXAMPLE 10

N-[4-(2,5-Dimethoxy-4-methylphenyl)-2-thiazolyl]-1-(carboxymethyl)indole-2-carboxamide (method H).

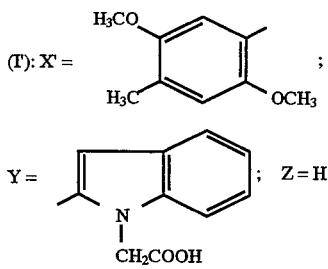

A mixture of 1.0 g of 2-amino-4-(2,5-dimethoxy-4-methylphenyl)thiazole, 1.09 g of N-(tert-butyoxycarbonylmethyl)-2-indolecarboxylic acid, 2.0 g of BOP and 0.55 ml of triethylamine in 5 ml of DMF is stirred at r.t. for 48 hours. The reaction mixture is poured into pH 2 buffer solution, and the precipitate formed is filtered off and washed with water. The precipitate is taken up with DCM, and the organic phase is washed with saturated sodium hydrogen carbonate solution and with pH 2 buffer solution, dried over magnesium sulphate and evaporated under vacuum. The residue is chromatographed on silica, eluting with a DCM/AcOEt (100:1.5; v/v) mixture. The tert-butyl ester obtained is taken up in 10 ml of TFA and left stirring for 3 hours at r.t. The mixture is evaporated under vacuum, the residue is taken up with 2N NaOH solution, the aqueous phase is washed with DCM and acidified by adding concentrated HCl, and the precipitate formed is filtered off and dried under vacuum in an oven. 1.4 g of the expected product, m.p.=206° C., are obtained.

EXAMPLE 11

N-[4-(4-Trifluoromethyl-2,6-dimethoxyphenyl)-2-thiazolyl]-1H-indole-2-carboxamide (method F).

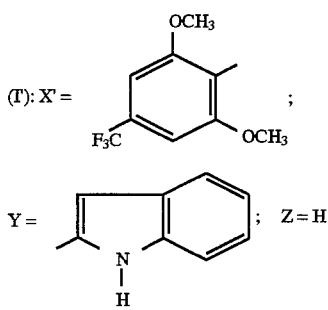

A mixture of 0.609 g of 2-amino-4-(4-trifluoromethyl-2,6-dimethoxyphenyl)thiazole, 0.447 g of N-acetyl-2-indolecarboxylic acid, 1.062 g of BOP and 0.243 g of triethylamine in 30 ml of DCM is stirred at r.t. for 48 hours. 100 ml of water are added, and the organic phase is separated after settling has taken place, dried over sodium sulphate and evaporated under vacuum. The derivative acetylated on the indole nitrogen which is obtained is taken up in 50 ml of MeOH, 2 g of sodium carbonate are added and the mixture is stirred overnight at r.t. It is evaporated under vacuum, the residue is taken up with 100 ml of water, the mixture is extracted with DCM, and the organic phase is dried over sodium sulphate and evaporated under vacuum. 0.54 g of the expected product is obtained after crystallization in DCM, m.p.>260° C.

EXAMPLE 12

N-[4-(4-Trifluoromethyl-2,6-dimethoxyphenyl)-2-thiazolyl]-1-(tert-butoxycarbonylmethyl)indole-2-carboxamide (method I).

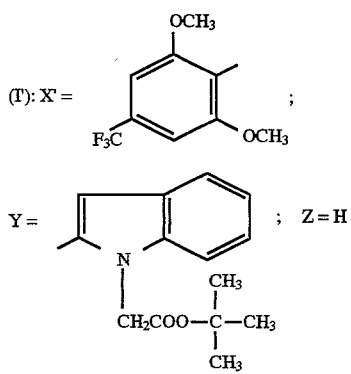

A mixture of 0.609 g of 2-amino-4-(4-trifluoromethyl-2,6-dimethoxyphenyl)thiazole, 0.606 g of N-(tert-butoxycarbonylmethyl)-2-indolecarboxylic acid, 1.062 g of BOP and 0.243 g of triethylamine in 30 ml of DCM is stirred at r.t. for 24 hours. 50 ml of water are then added, and the organic phase is separated after settling has taken place, dried over sodium sulphate and evaporated under vacuum. The residue is chromatographed on silica H, eluting with a DCM/AcOEt (100:5; v/v) mixture. 0.79 g of the expected product is obtained after crystallization in ether, m.p.= 214°–216° C.

EXAMPLE 13

N-[4-(4-Trifluoromethyl-2,6-dimethoxyphenyl)-2-thiazolyl]-1-(carboxymethyl)indole-2-carboxamide trifluoroacetate (method J).

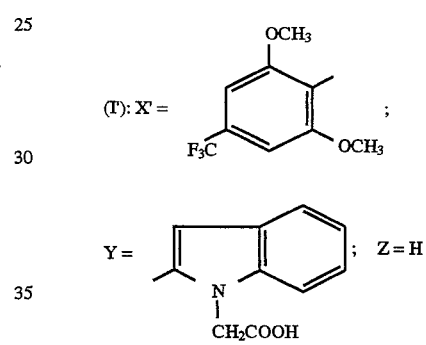

20 ml of TFA are cooled to 10° C., 0.5 g of the compound obtained in EXAMPLE 12 is added and the mixture is left stirring for 3 hours at 10° C. It is evaporated under vacuum, the residue is taken up with water, the mixture is extracted with AcOEt, and the organic phase is dried over sodium sulphate and evaporated under vacuum. 0.47 g of the expected product is obtained after crystallization in ether, m.p.=230°–232° C.

Employing the procedures described above, the compounds of formula (I') described in TABLE IV below are prepared.

TABLE IV (structure: Z-C(S)(=N-...)-X' with NH-CO-indole, indole N-R)

| Example No. | X' | Z | R | M.P.; °C. base or salt | Method used |
|---|---|---|---|---|---|
| 14 | 4-Cl-2,6-(OCH₃)₂-phenyl | H | H | 280 | A |
| 15 | 2-OCH₃-4-CH₃-6-OCH₃-phenyl | H | —COCH₃ | 214 | A |
| 16 | 2,4,5-tri(OCH₃)-phenyl | H | H | 275 | A |
| 17 | 2-Cl-3,4,6-tri(OCH₃)-phenyl | H | H | 236 | E |
| 18 | 2-OCH₃-3-CH₃-4-OCH₃-6-CH₃-pyridyl | H | H | 283–285 | A |
| 19 | 2-OCH₃-4-OCH₃-5-CH₃-6-OCH₃-pyrimidinyl | H | H | 2HCl 283–285 | A |
| 20 | 2-OCH₃-4-Cl-5-CH₃-6-OCH₃-pyrimidinyl | H | H | 284–286 | A |
| 21 | 2-Cl-4-CH₃-5-OCH₃-phenyl (with CH₃) | H | H | 300 | F |
| 22 | 2-Cl-4-CH₃-5-OCH₃-phenyl (with CH₃) | —CH₃ | H | 261 | F |
| 23 | 2-OCH₃-4-CH₃-5-OCH₃-phenyl | H | H | 279 | F |

TABLE IV-continued
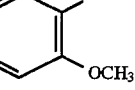
| Example No. | X' | Z | R | M.P.; °C. base or salt | Method used |
|---|---|---|---|---|---|
| 24 | H3CO—/—CH3 ; H3C—/—OCH3 (2,5-dimethoxy-4-methylphenyl) | —CH3 | H | 281 | F |
| 25 | H3CO—/—CH3 ; H3C—/—OCH3 | —CH3 | —CH2COOH | 223 | H |
| 26 | H3C—/—CH3 ; H3CO—/—OCH3 | H | H | 1H2O 279–280 | F |
| 27 | H3C—/—CH3 ; H3CO—/—OCH3 | —CH3 | H | 267 | F |
| 28 | H3C—/—CH3 ; H3CO—/—OCH3 | —CH3 | —CH2COOH | 1/2TFA 204 | G |
| 29 | H3CH2C—/—CH3 ; H3CO—/—OCH3 | —CH3 | H | 267 | F |
| 30 | H3CO—/—CH3 ; H3CO—/—OCH3 | —CH3 | H | 240 | A |
| 31 | H3CO—/—CH3 ; H3CO—/—OCH3 | —CH3 | —CH2CO2t-Bu | 140–150 | I |
| 32 | H3CO—/—CH3 ; H3CO—/—OCH3 | —CH3 | CH2COOH | 1/2TFA, 1 H2O 174–180 | J |
| 33 | H3CO—/—OCH3 | —CH2—C6H5 | H | 1/2H2O 201 | F |
| 34 | H3CO—/—OCH3 | —CH2CH2CH3 | H | 210 | A |

We claim:

1. A method for the treatment of pathologies necessitating the stimulation of the cholecystokinin-A receptors by a total or partial agonist effect comprising aministering to a man in need thereof a compound of formula:

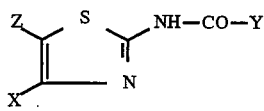 (I)

in which Y is a radical selected from the group consisting of a 3-quinolyl group and a 2-indolyl group of formula;

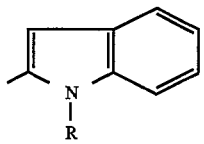

in which:

R is selected from the group consisting of hydrogen, acetyl and —$CH_2COOR'$, R' being selected from the group consisting of hydrogen and $C_1$–$C_4$-alkyl;

X is selected from the group consisting of 4-chloro-2,6-dimethoxyphenyl, 2,6-dimethoxy-4-methylphenyl, 2,4,5-trimethoxyphenyl, 4-methyl-2,3,6-trimethoxyphenyl, 2,6-dimethoxy-4-ethylphenyl, 2,4,6-trimethoxy-5-chlorophenyl, 2,4,6-trimethoxy-3-pyridyl, 2,4-dimethoxy-6-methyl-3-pyridyl, 6-chloro-2,4-dimethoxy-5-pyrimidinyl, 2,4,6-trimethoxy-5-pyrimidinyl, 5-chloro-2,4-dimethoxyphenyl, 5-chloro-2-methoxy-4-methylphenyl, 2,5-dimethoxy-4-methylphenyl, 4-trifluoromethyl-2,6-dimethoxyphenyl, 2,4-dimethoxy-5-methylphenyl, 5-ethyl-2,4-dimethoxyphenyl and 2,4-dimethoxyphenyl groups;

Z is selected from the group consisting of H, $C_1$–$C_4$-alkyl and benzyl;

with the proviso that Z is necessarily hydrogen when X is a phenyl radical substituted simultaneously at positions 2 and 6 or when X is a 3-pyridyl radical substituted simultaneously at positions 2 and 4 or when X is a 5-pyrimidinyl radical substituted simultaneously at positions 4 and 6;

as well as its pharmaceutically acceptable salts and its solvates.

2. A method for the treatment of pathologies necessitating the stimulation of the cholecystokinin-A receptors by a total or partial agonist effect comprising administering to a man in need thereof a compound of formula:

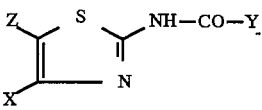 (I)

in which Y is radical selected from the group consisting of a 3-quinolyl group and a 2-indolyl group of formula;

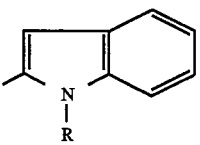

in which:

R is selected from the group consisting of hydrogen, acetyl and —$CH_2COOR'$, R' being selected from the group consisting of hydrogen and $C_1$–$C_4$-alkyl;

X is selected from the group consisting of 2,6 dimethoxy-4-ethylphenyl, and 2,4-dimethoxyphenyl groups;

Z is selected from the group consisting of H, $C_1$–$C_4$ alkyl and benzyl;

with the proviso that Z is necessarily hydrogen when X is 2,6-dimethoxy-4-ethylphenyl as well as its pharmaceutically acceptable salts and its solvates.

3. A method according to claim 2, comprising the administration to a man in need thereof of a compound of formula (I) in which Y and R are as defined in claim 2;

X is 2,6-dimethoxy-4-ethylphenyl;

Z represents H as well as its pharmaceutically acceptable salts and its solvates.

* * * * *